US012642619B2

(12) United States Patent
Boyle

(10) Patent No.: US 12,642,619 B2
(45) Date of Patent: Jun. 2, 2026

(54) FACE SHIELD APPARATUSES AND SYSTEMS INCLUDING SAME

(71) Applicant: The Research Foundation for the State University of New York, Albany, NY (US)

(72) Inventor: Nariman Boyle, Setauket, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 458 days.

(21) Appl. No.: 18/021,316

(22) PCT Filed: Aug. 16, 2021

(86) PCT No.: PCT/US2021/046083
§ 371 (c)(1),
(2) Date: Feb. 14, 2023

(87) PCT Pub. No.: WO2022/036305
PCT Pub. Date: Feb. 17, 2022

(65) Prior Publication Data
US 2023/0301742 A1 Sep. 28, 2023

Related U.S. Application Data

(60) Provisional application No. 63/065,702, filed on Aug. 14, 2020.

(51) Int. Cl.
*A61B 90/00* (2016.01)
*A61B 46/20* (2016.01)
(Continued)

(52) U.S. Cl.
CPC .............. *A61B 90/05* (2016.02); *A61B 46/20* (2016.02); *A61G 13/121* (2013.01); *A61F 9/007* (2013.01)

(58) Field of Classification Search
CPC ......... A61B 90/05; A61B 90/40; A61B 90/14; A61B 90/17; A61B 46/20; A61B 46/23;
(Continued)

(56) References Cited

U.S. PATENT DOCUMENTS 4,122,848 A 10/1978 Carpel
4,213,169 A 7/1980 Kempkers
(Continued)

FOREIGN PATENT DOCUMENTS

CN 203277706 U 11/2013
CN 211059756 U 7/2020
(Continued)

*Primary Examiner* — Daniel A Miller
(74) *Attorney, Agent, or Firm* — Garrett Smith

(57) ABSTRACT
Face shield apparatuses used during medical procedures. The apparatuses may include a frame including a first and second curved member. Each of the first and second curved members may include: a first end, a second end, and an outer surface extending between the first and second end. The apparatuses may also include a bridge extending between the first end of the first curved member and the first end of the second curved member, a first rib(s) and second rib(s) rotatably coupled to the outer surface of the first curved member and second curved member, respectively. The rib(s) may extend beyond and substantially parallel to the outer surface of the first and second curved members. Additionally, the apparatuses may further include a first and second extension coupled to the first and second curved members, and a backing component releasably coupled to the first and second extensions.

20 Claims, 16 Drawing Sheets

(51) Int. Cl.
    *A61F 9/007*     (2006.01)
    *A61G 13/12*     (2006.01)

(58) Field of Classification Search
    CPC ...... A61B 2090/101; A61B 2090/3954; A61G 13/121; A61G 13/10; A61G 10/005; A61G 10/04; A47C 21/024
    USPC .......................................................... 128/849
    See application file for complete search history.

(56) References Cited

U.S. PATENT DOCUMENTS

| | | | |
|---|---|---|---|
| 4,821,340 A | 4/1989 | Johnson | |
| 4,965,887 A | 10/1990 | Paoluccio et al. | |
| 5,220,699 A | 6/1993 | Farris | |
| 5,941,021 A | 8/1999 | Valls, Jr. et al. | |
| 6,068,335 A | 5/2000 | Glover | |
| 6,662,421 B1 | 12/2003 | Krippelz, Sr. et al. | |
| 7,093,331 B1 | 8/2006 | Holmberg et al. | |
| 8,225,421 B1 | 7/2012 | Froissard | |
| 8,360,081 B2 | 1/2013 | Zweideck | |
| 8,863,944 B2 | 10/2014 | Maclachlan | |
| 11,384,866 B2 | 7/2022 | Zhang et al. | |
| 11,607,021 B2 | 3/2023 | Haythornthwaite | |
| 2004/0260311 A1* | 12/2004 | Bourel ................... | A61B 90/14 606/130 |
| 2005/0268952 A1 | 12/2005 | Ma | |
| 2006/0086025 A1 | 4/2006 | Benedict et al. | |
| 2006/0137322 A1 | 6/2006 | Moehnke et al. | |
| 2010/0143048 A1 | 6/2010 | Lin | |
| 2013/0258205 A1 | 10/2013 | Kawasaki et al. | |
| 2014/0252189 A1 | 9/2014 | Kifer et al. | |
| 2016/0230393 A1 | 8/2016 | Huber | |
| 2018/0195288 A1 | 7/2018 | Huber | |
| 2020/0288829 A1 | 9/2020 | Haythornthwaite | |
| 2020/0318422 A1 | 10/2020 | Koster et al. | |
| 2020/0378126 A1 | 12/2020 | Huber | |
| 2022/0025653 A1 | 1/2022 | Huber | |
| 2022/0031095 A1 | 2/2022 | Spiro et al. | |
| 2023/0051107 A1 | 2/2023 | Liu et al. | |

FOREIGN PATENT DOCUMENTS

| | | | |
|---|---|---|---|
| CN | 111868396 A | 10/2020 | |
| CN | 112833307 A | 5/2021 | |
| CN | 215181415 U | 12/2021 | |
| CN | 114268864 A | 4/2022 | |
| CN | 109675166 A | 7/2022 | |
| CN | 216915622 U | 7/2022 | |
| CN | 112277140 B | 8/2022 | |
| CN | 115561928 A | 1/2023 | |
| DE | 102018110788 A1 | 12/2018 | |
| DE | 112019003148 T5 | 3/2021 | |
| EP | 2264352 | 12/2010 | |
| EP | 3697065 B1 | 9/2021 | |
| EP | 4072110 A1 | 10/2022 | |
| GB | 1158476 A | 7/1969 | |
| JP | 2008502939 | 1/2008 | |
| JP | 2008506081 A | 2/2008 | |
| JP | 2008542654 A | 11/2008 | |
| JP | 2008545503 A | 8/2012 | |
| JP | 5260161 B2 | 8/2013 | |
| JP | 2013540037 | 10/2013 | |
| JP | 2017502710 A | 1/2017 | |
| JP | 2020054882 A | 4/2020 | |
| KR | 20160002938 U | 8/2016 | |
| KR | 20200099054 A | 8/2020 | |
| WO | 2020093814 A1 | 5/2020 | |
| WO | 2021141320 A1 | 7/2021 | |
| WO | 2021202018 A1 | 10/2021 | |
| WO | 2022098722 | 5/2022 | |

* cited by examiner

FACE SHIELD APPARATUSES AND SYSTEMS INCLUDING SAME

CROSS-REFERENCE TO RELATED APPLICATIONS

This application claims priority to U.S. provisional application No. 63/065,702 filed on Aug. 14, 2020, the content of which is hereby incorporated by reference into the present application

BACKGROUND

The disclosure relates generally to medical apparatuses, and more particularly, to face shield apparatuses and systems including face shield apparatuses that may be used during medical/surgical procedures.

When performing ocular-based (e.g., eye, eyelid) or upper facial surgeries it is crucial to maintain sterilization for the area of the patient's face undergoing the surgery. Conventionally, surgeons cover a portion of the patient's face with a surgical towel or surgical plastic coverings to isolate the area of the patient in which surgery is being performed on. In conventional procedures, the surgical towel or plastic may simply be positioned directly on and directly over a portion of the patient's face. Additionally, the surgical towel or surgical plastic is typically taped or secured to the patient's face using adhesive to maintain sterilization during the procedure. However, the conventional procedure of taping/adhering the towel or plastic to the patient does not always guarantee sterilization during the surgical procedure. During the surgery, the surgical towel or plastic may slide or get in the way of the surgeon performing the surgical procedure. As such, the surgeon often has to adjust or move the surgical towel during the procedure.

Additionally, under conventional procedures, access to other surgically required components, such as an oxygen mask for the patient, are difficult to access. As a result of the towel/plastic resting directly on the patient's face in conventional procedures, the patient may re-breath $CO_2$ and the anesthesiologist often has a difficult time accessing certain component (e.g., the oxygen mask). For example, the anesthesiologist needing to access the oxygen mask must either lift the towel or plastic, which reduces the chance of successful sterilization practices, and/or must attempt to adjust the mask blindly and/or maneuver around a surgical towel or plastic sheet resting up on the patients face and oxygen mask. Conventional procedures include many difficulties for the attending surgeons, anesthesiologist, nurses, and/or operating room (OR) technicians.

BRIEF DESCRIPTION

A first aspect of the disclosure provides a face shield apparatus, including: a frame including a first curved member and a second curved member positioned opposite the first curved member, each of the first curved member and the second curved member including: a first end; a second end positioned opposite the first end; and an outer surface extending between the first end and the second end; a bridge extending between the first end of the first curved member and the first end of the second curved member; at least one first rib rotatably coupled to the outer surface of the first curved member, the at least one first rib extending beyond and substantially parallel to the outer surface of the first curved member; at least one second rib rotatably coupled to the outer surface of the second curved member, the at least one second rib extending beyond and substantially parallel to the outer surface of the second curved member; a first extension coupled to the first curved member, adjacent the second end of the first curved member; a second extension coupled to the second curved member, adjacent the second end of the second curved member; and a backing component releasably coupled to the first extension and the second extension, the backing component including: at least two openings, the at least two openings receiving one of the first extension or the second extension.

A second aspect of the disclosure provides a face shield system, including: a face shield apparatus including: a frame including a first curved member and a second curved member positioned opposite the first curved member, each of the first curved member and the second curved member including: a first end; a second end positioned opposite the first end; and an outer surface extending between the first end and the second end; a bridge extending between the first end of the first curved member and the first end of the second curved member; at least one first rib rotatably coupled to the outer surface of the first curved member, the at least one first rib extending beyond and substantially parallel to the outer surface of the first curved member; at least one second rib rotatably coupled to the outer surface of the second curved member, the at least one second rib extending beyond and substantially parallel to the outer surface of the second curved member; a first extension coupled to the first curved member, adjacent the second end of the first curved member; a second extension coupled to the second curved member, adjacent the second end of the second curved member; and a backing component releasably coupled to the first extension and the second extension, the backing component including: at least two openings, the at least two openings receiving one of the first extension or the second extension; and a surgical drape positioned over and contacting at least the frame, the at least one first rib, and the at least one second rib, respectively.

A third aspect of the disclosure provides a face shield apparatus, including: a curved frame including: a first end; a second end positioned opposite the first end; an outer surface extending between the first end and the second end; a bridge formed between the first end and the second end; and a plurality of ribs extending beyond and substantially parallel to the outer surface of the curved frame; and a backing component releasably coupled to the first end of the curved frame and the second end of the curved frame, the backing component including: at least two openings, the at least two openings receiving one of the first end of the curved frame and the second end of the curved frame.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION

As an initial matter, in order to clearly describe the current disclosure, it will become necessary to select certain terminology when referring to and describing relevant components within the disclosure. When doing this, if possible, common industry terminology will be used and employed in a manner consistent with its accepted meaning. Unless otherwise stated, such terminology should be given a broad interpretation consistent with the context of the present application and the scope of the appended claims. Those of ordinary skill in the art will appreciate that often a particular component may be referred to using several different or overlapping terms. What may be described herein as being a single part may include and be referenced in another context as consisting of multiple components. Alternatively, what may be described herein as including multiple components may be referred to elsewhere as a single part.

As discussed herein, the disclosure relates generally to medical apparatuses, and more particularly, to face shield apparatuses and systems including face shield apparatuses that may be used during medical/surgical procedures.

These and other embodiments are discussed below with reference to FIGS. 1-13B. However, those skilled in the art will readily appreciate that the detailed description given herein with respect to these Figures is for explanatory purposes only and should not be construed as limiting.

Figure 1:
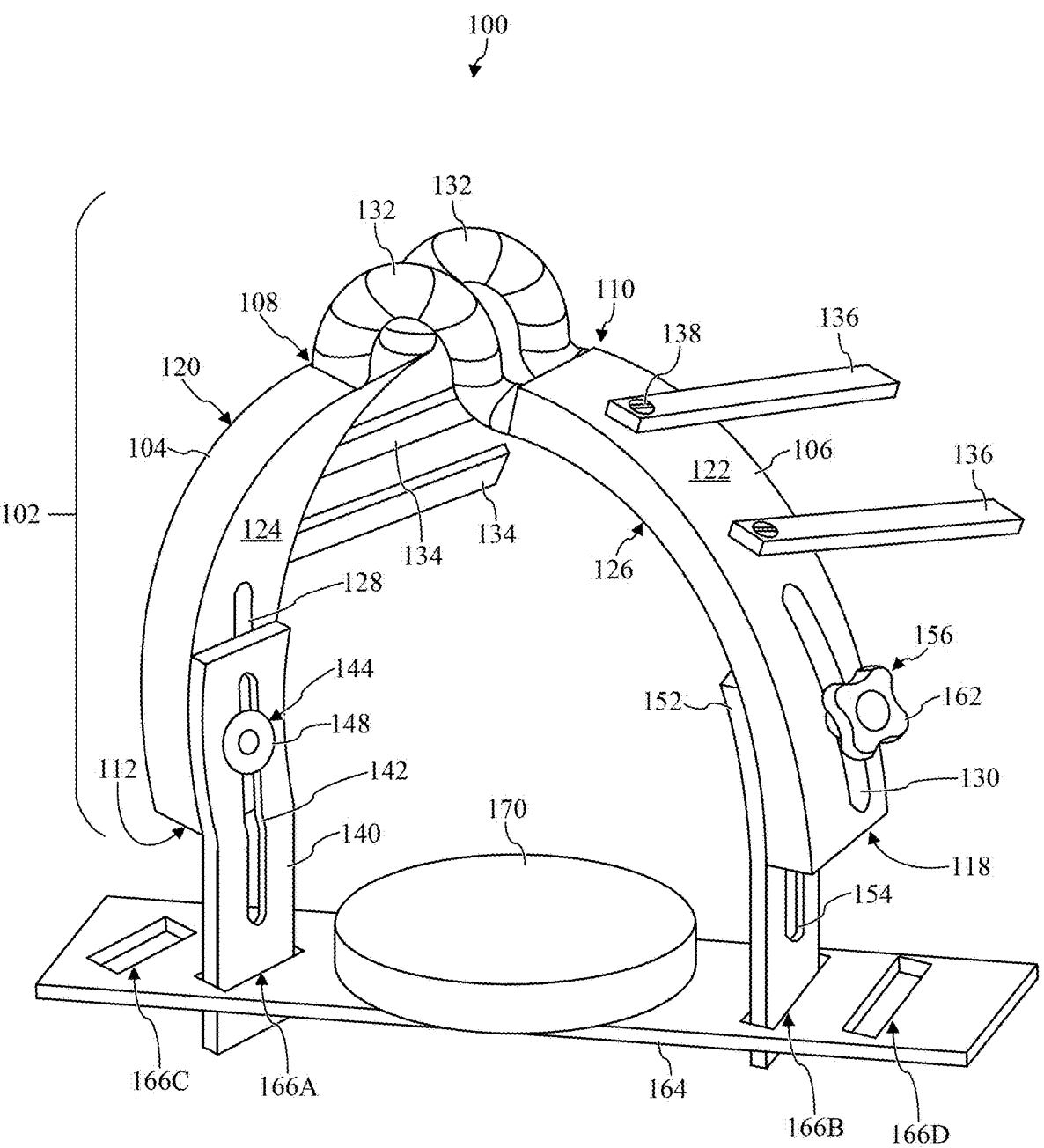
FIG. 1 shows a perspective view of a face shield apparatus used during medical procedures, according to embodiments of the disclosure.
Figure 2:
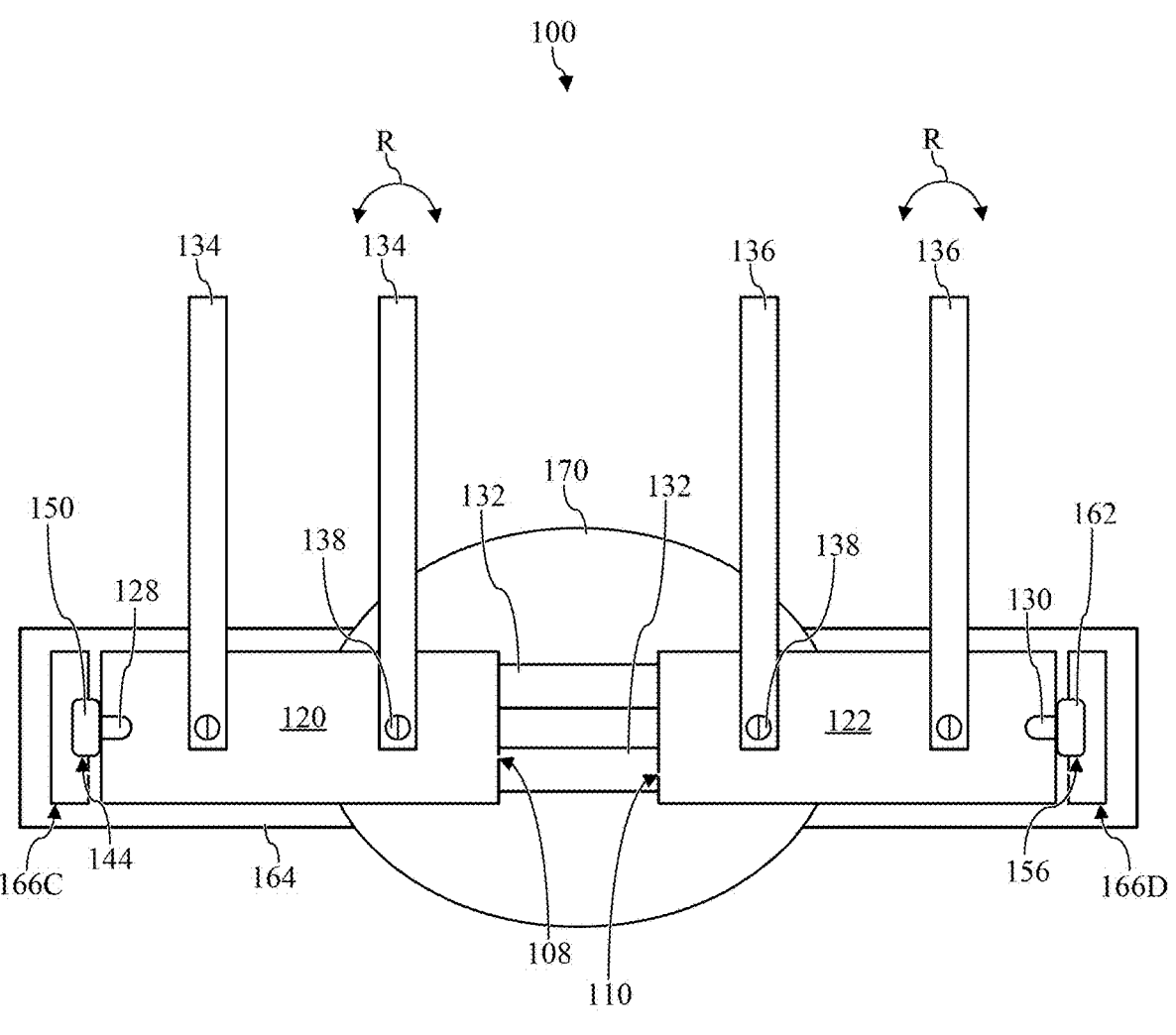
FIG. 2 shows a top view of the face shield apparatus of FIG. 1, according to embodiments of the disclosure.
Figure 3:
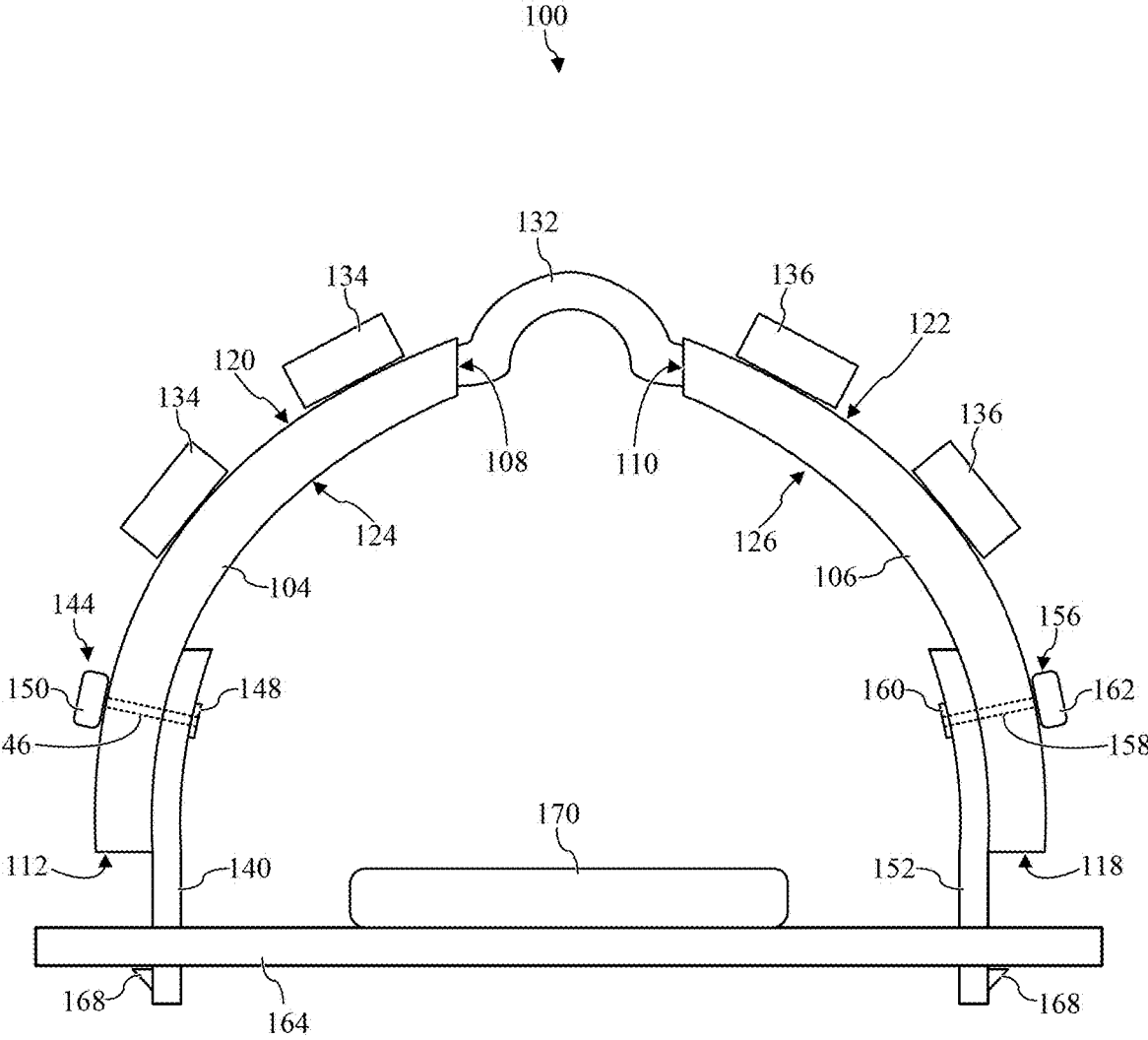
FIG. 3 shows a back view of the face shield apparatus of FIG. 1, according to embodiments of the disclosure.
Figure 4:
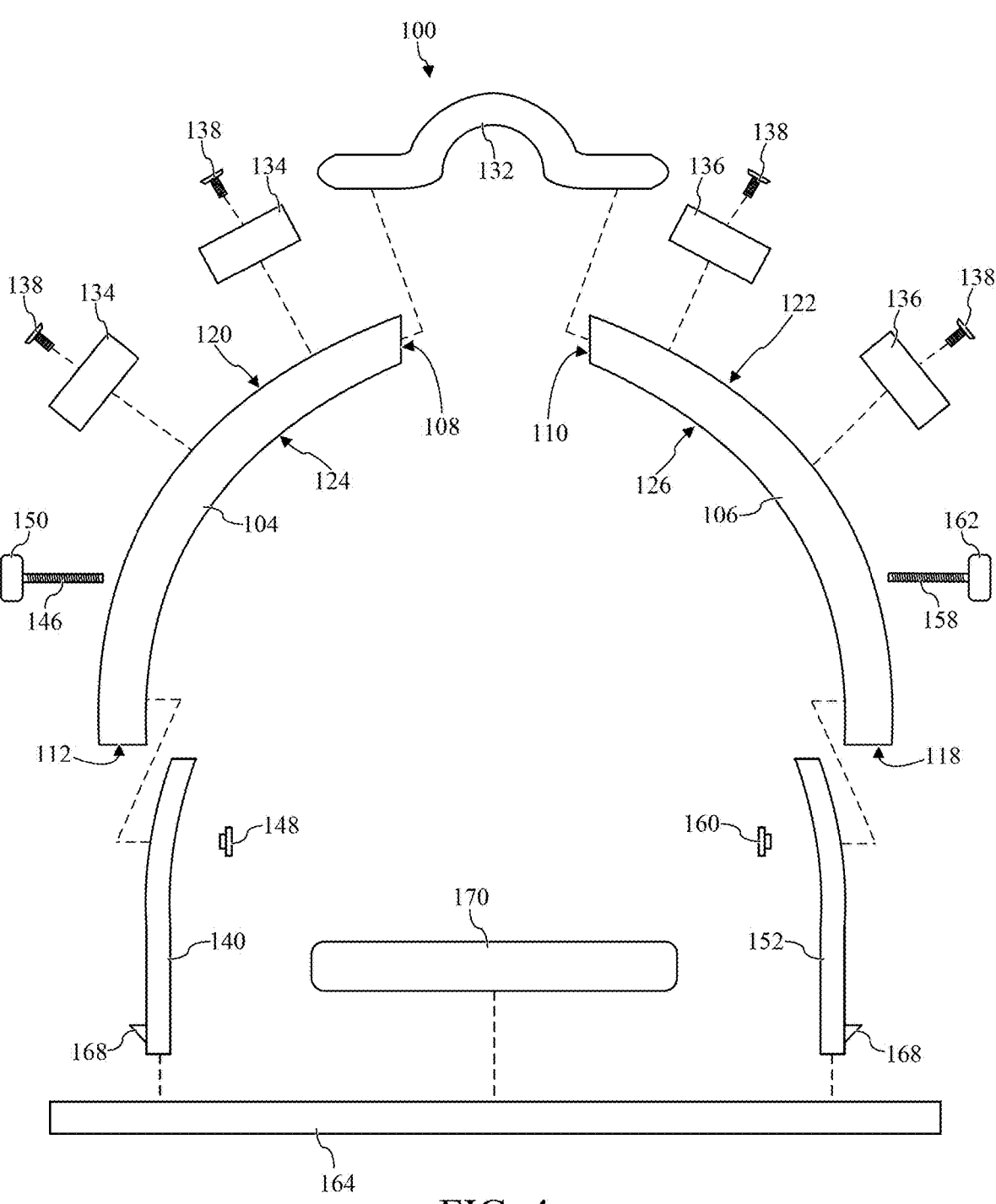
FIG. 4 shows an exploded back view of the face shield apparatus of FIG. 1, according to embodiments of the disclosure.

FIGS. 1-4 show various views of a face shield apparatus 100 according to a non-limiting example. More specifically, FIG. 1 shows a perspective view of face shield apparatus 100, FIG. 2 shows a top view of face shield apparatus 100, FIG. 3 shows a back view of face shield apparatus 100, and FIG. 4 shows a back exploded view of face shield apparatus 100.

Face shield apparatus 100 may include a frame 102. Frame 102 may include a first curved member 104 and a second curved member 106 positioned opposite first curved member 104. First curved member 104 and second curved member 106 may also be spaced apart and/or distanced from one another in apparatus 100. In the non-limiting example shown in FIGS. 1-4, each of first curved member 104 and second curved member 106 may include a first end 108, 110 and a second end 112, 118 positioned opposite first end 108, 110. Additionally, first curved member 104 and second curved member 106 may include outer surface 120, 122 extending between first end 108, 110 and second end 112, 118. Positioned opposite curved outer surface 120, 122 may also be an inner surface 124, 126. Frame 102, and more specifically first curved member 104 and second curved member 106 may be formed from any suitable material that may be substantially rigid and/or maintain the curved structure or configuration as shown here in. For example, first curved member 104 and second curved member 106 forming frame 102 may be formed from any suitable polymer, metal, metal alloy, ceramic, or similar material including similar material characteristics/properties. As discussed herein, the curved shape of frame 102, as well as the space between inner surfaces 124, 126 of first curved member 104 and second curved member 106 in distinct portions of face shield apparatus 100, may allow a patient's head to be positioned substantially within and/or substantially covered by face shield apparatus 100.

Additionally, as shown in FIG. 1, each of first curved member 104 and second curved member 106 of frame 102 may include an aperture 128, 130 extending therethrough. More specifically, aperture 128 may extend through outer surface 120 and inner surface 124 of first curved member 104. Moreover, aperture 130 may extend through outer surface 122 and inner surface 126 of second curved member 106 of frame 102. In the non-limiting example, apertures 128, 130 may be formed substantially adjacent second end 112, 118 of the respective first curved member 104 and second curved member 106. As discussed herein, apertures 128, 130 formed in first curved member 104 and second curved member 106 may aid in coupling first curved member 104 and second curved member 106 to distinct components/portions of face shield apparatus 100, as well as aid in adjusting the height of frame 102 for face shield apparatus 100.

Face shields apparatus 100 may also include a bridge 132 couple to and/or formed within frame 102. More specifically, bridge 132 may extend between and/or positioned directly adjacent first end 108 of first curved member 104 and first end 110 of second curved member 106. In the non-limiting example shown in FIGS. 1 and 2, bridge 132 may be formed as two distinct tubes extending between first end 108 of first curved member 104 and first end 110 of second curved member 106. However, it is understood that bridge 132 of face shield apparatus 100 may be formed in any suitable configuration to receive and/or cradle a patient's nose, as discussed herein. In one non-limiting example, bridge 132 may be formed from a substantially flexible material including, but not limited to, polymers, coated metals/metal alloys, natural fibers, or similar materials. In this example, the shape of bridge 132 may be adjusted to correspond and/or correlate to each individual patient's nose shape. In another non-limiting example, bridge 132 may be formed from a substantially rigid and/or stiff material. When formed from a rigid material, the shape or configuration of bridge 132 may be substantially fixed or permanent. As such, the shape of fixed bridge 132 may be sized to accommodate or receive nearly any size and/or shaped nose of a patient.

As shown in FIGS. 1-4, face shield apparatus 100 may also include a plurality of ribs 134, 136. More specifically, at least one first rib 134 may be rotatably coupled to outer surface 120 of first curved member 104, and at least one second rib 136 may be rotatably coupled to outer surface 122 of second curved member 106. In the non-limiting example, first rib(s) 134 may extend beyond and substantially parallel to outer surface 120 of first curved member 104. Similarly, second rib(s) 136 may extend beyond and substantially parallel to outer surface 122 of second curved member 106. A portion of each rib(s) 134, 136 may be disposed over, directly contact, and/or positioned on respective outer surfaces 120, 122 for each curved member 104, 106. The remainder of each rib(s) 134, 136 may hangover or extend beyond frame 102 and the various portions/components forming frame 102. As shown, each rib(s) 134, 136 may be rotatably coupled to first curved member 104 or second curved member 106 using a single screw 138. However, it is understood that ribs 134, 136 may be coupled to first curved member 104 or second curved member 106 using any suitable coupling technique and/or mechanism (see, FIG. 7). As a result of rotatably coupling ribs 134, 136 to frame 102 of face shield apparatus 100, each rib 134, 136 may rotate in a direction (R) independently of one another. As discussed herein, ribs 134, 136 may support a surgical drape positioned over a patient's face when performing a medical/surgical procedure. In order to support surgical drapes during the procedure, ribs 134, 136 may be formed from any suitable rigid and/or stiff material. For example, ribs 134, 136 may be formed from hardened polymers, metal, metal alloys, ceramics, or similar materials having similar material characteristics. Two first ribs 134 and two second ribs 136 are shown in the non-limiting example. It is understood that the number of ribs 134, 136 shown are illustrative. As such, face shield apparatus 100 may include more or less ribs 134, 136 then shown and discussed herein.

As shown in FIGS. 1-4, face shield apparatus 100 may also include a first extension 140. first extension 140 may be coupled to first curved member 104. More specifically, first extension 140 may be coupled to first curved member 104 adjacent second end 112 a first curved member 104. In the non-limiting example, a portion of first extension 140 may also contact inner surface 124 of curved member 104 adjacent second end 112. First extension 140 may extend down/beyond second end 112 of first curved member 104 and may be coupled and/or may interact with additional components of face shield apparatus 100, as discussed herein. First extension 140 may be formed from any suitable material that may support first curved member 104 and/or provide support to frame 102 when used during medical procedures discussed herein. That is, and as discussed herein, first extension 140 make contact or be positioned on a procedure table/chair during the medical procedure, and thus must include substantially rigid and/or stiffness properties to support frame 102 of face shield apparatus 100. In non-limiting examples, first extension 140 may be formed from polymers, metals, metal alloys, ceramics, or any other suitable material having similar material characteristics/properties.

First extension 140 may also include a hole 142 extending therethrough. As shown in FIG. 1, hole 142 may extend or be formed through a portion of first extension 140 that is positioned adjacent to and/or contacts first curved member 104. Additionally, as shown, hole 142 of first extension 140 may be substantially aligned, at least a partially concentric, and/or correspond to aperture 128 formed through first curved member 104. Aligned aperture 128 of first curved member 104 and hole 142 of first extension 140 may aid in the coupling of first extension 140 to first curved member 104, as well as may adjust/maintain a height of frame 102 during the medical procedure using face shield apparatus 100, as discussed herein.

In a non-limiting example as shown in FIGS. 1-3, a first fastener 144 may extend through hole 142 of first extension 140 and aperture 128 of first curved member 104. First fastener 144 may allow for adjustment in the height of frame 102 when loosened and/or removed from hole 142/aperture 128. Additionally, first fastener 144 may releasably couple and/or secure first extension 140 to first curved member 104 to maintain or fix frame 102 at a predetermined height when performing the medical procedure, as discussed herein. In the non-limiting example, first fastener 144 may be formed as a threaded bolt 146 and locking nut 148. Threaded bolt 146 may include a handle or dial 150 that may be positioned directly adjacent outer surface 120 of first curved member 104 when threaded bolt 146 is inserted through aperture 128 and hole 142, respectively. To secure or fix first curved member 104 in a predetermined position (e.g., height) dial 150 and threaded bolt 146 may be turned, rotated, or tightened using locking nut 148 until dial 150 and locking nut 148 provide a compressive force onto curved member 104 and first extension 140. Although shown as including a threaded bolt 146 and locking nut 148, it is understood that first fastener 144 of face shield apparatus 100 may be formed as any suitable adjustable fastener/coupling component, device, and/or assembly. For example, first fastener 144 may be formed as a ratchet assembly, a pin assembly configured to be inserted into a plurality of concentric holes 142 and apertures 128, a pair of corresponding magnets each positioned on first curved member 104 and first extension 140, a compression spring locking mechanism extending through hole 142 and aperture 128, or any other suitable component/assembly.

Face shield apparatus 100 may also include a second extension 152. Second extension 152 may be coupled to second curved member 106. More specifically, second extension 152 may be couples to second curved member 106 adjacent second end 118 of second curved member 106. In the non-limiting example, a portion of second extension 152 may also contact inner surface 126 of second curved member 106, adjacent second end 118. Second extension 152 may extend down/beyond second end 118 of second curved member 106 and may be coupled and/or may interact with additional components of face shield apparatus 100, as discussed herein. Similar to first extension 140, second extension 152 may be formed from any suitable material that may support second curved member 106 and/or provide support to frame 102 when used during medical procedures discussed herein. That is, and as discussed herein, second extension 152 make contact or be positioned on a procedure table/chair during the medical procedure, and thus must include substantially rigid and/or stiffness properties to support frame 102 of face shield apparatus 100. In non-limiting examples, second extension 152 may be formed from polymers, metals, metal alloys, ceramics, or any other suitable material having similar material characteristics/ properties.

Also similar to first extension 140, second extension 152 may include a hole 154 extending therethrough. As shown in FIG. 1, hole 154 may extend or be formed through a portion of second extension 152 that is positioned adjacent to and/or contacts second curved member 106. Additionally as shown, hole 154 of second extension 152 may be substantially aligned, at least partially concentric, and/or correspond to aperture 130 formed through second curved member 106. Aligned aperture 130 of second curved member 106 and hole 154 of second extension 152 may aid in the coupling of second extension 152 and second curved member 106, as well as may adjust/maintain a height of frame 102 during the medical procedure using face shield apparatus 100.

In a non-limiting example as shown in FIGS. 1-3, a second fastener 156 may extend through hole 154 of second extension 152 and aperture 130 of second curved member 106. Second fastener 156 may allow for adjustment in the height a frame 102 when loosened and/or removed from hole 154/aperture 130. Additionally, second fastener 156 may releasably couple and/or secure second extension 152 to second curved member 106 to maintain or fix frame 102 at a predetermined height when performing the medical procedure, as discussed herein. In the non-limiting example, second fastener 156 may be substantially similar to first fastener 144, and may be formed as a threaded bolt 158, locking nut 160, and dial 162. Second fastener 156 may function or operation substantially similar to first fastener 144 as discussed herein. As such, redundant explanation of this component is omitted for clarity and brevity. Further, although shown as including a threaded bolt 158 and locking nut 160, it is understood that second fastener 156 of face shield apparatus 100 may be formed as any suitable adjustable fastener/coupling component, device, and/or assembly—similar to those discussed herein with respect to first fastener 144.

Face shield apparatus 100 may also include a backing component 164. Backing component 164 may be releasably coupled to first extension 140 and second extension 152, respectively. In the non-limiting example shown in FIGS. 1 and 2, backing component 164 may include at least two openings 166 formed therethrough. That is, backing component 164 may include openings 166 formed adjacent opposing ends for receiving first extension 140 and/or second extension 152. As shown, an end of first extension 140, opposite hole 142, may pass through a single opening 166A formed through backing component 164, while an end of second extension 152, opposite hole 154, may pass through a distinct opening 166B formed through backing component 164. To adjust a width of frame 102 first extension 140 and second extension 152 may be removed from openings 166A, 166B and inserted into openings 166C, 166 D, respectively. As a result of the flexible characteristics and/or extendibility (see, FIG. 8) of bridge 132, the width of frame 102 (e.g., the space between first curved member 104 and second curved member 106) may be readily adjusted based on the size/width of the patient's face or head. Backing component 164 may be formed from any suitable material that may be substantially flexible and elastic. for example, backing component 164 may be formed from polymers or natural fibers.

As discussed herein, backing component 164 may be releasably coupled to first extension 140 and second extension 152. To maintain the coupling, first extension 140, second extension 152, and/or backing component 164 may include at least one coupling component 168. In the non-limiting example, first extension 140 and second extension 152 may each include coupling component 168. Specifically, and with reference to FIGS. 3 and 4, a ratchet style coupling component 168 may be formed on both first extension 140 and second extension 152. Ratchet style coupling component 168 may be formed on first extension 140/second extension 152 opposite second end 112, 118 of first curved member 104/second curved member 106. As shown, ratchet style coupling component 168 formed on first extension 140 may pass through opening 166A of backing component 164, and ratchet style coupling component 168 formed on second extension 152 may pass through opening 166B of backing component 164. Once respective coupling components 168 passed through openings 166A, 166B of backing component 164, first extension 140 and second extension 152 may be releasably coupled and/or secured to backing component 164. A flat shelf of each coupling component 168 may abut or contact backing component 164, adjacent openings 166A, 166B, to prevent the undesired uncoupling of first extension 140/second extension 152 and backing component 164. To release or uncouple first extension 140/second extension 152 and backing component 164, a user (e.g., doctor, physician, nurse, OR technician) may apply a force to backing component 164, adjacent openings 166, to deform (e.g., enlarge) openings 166. In turn, coupling component 168 and first extension 140/second extension 152 may then be removed from openings 166. Although shown and discussed herein as a ratchet style coupling component, it is understood that coupling component 168 of face shield apparatus 100 may be formed as any suitable coupling component, device, and/or assembly that may allow for the releasable coupling of first extension 140/second extension 152 and backing component 164.

As discussed herein, the back of a patient's head/neck may rest upon backing component 164 when implementing face shield apparatus 100 during the medical procedure. To support and/or provide comfort to the patient, face shield apparatus 100/backing component 164 may include a cushion 170. Cushion 170 may be positioned on backing component 164, between openings 166 formed therein. cushion 170 may be formed from any suitable material or assembly that may provide support and/or comfort to a patient substantially covered by face shield apparatus 100 during a medical procedure. In non-limiting examples, cushion 170 may be formed as a pillow-type support, or a gel pad. For maintaining sterilization or desired medical hygiene, cushion 170 may be releasably coupled to backing component 164 in order for cushion 170 to be removed, sterilized, and/or disposed of as desired.

Figure 5:
FIG. 5 shows a top view of a face shield system including the apparatus of FIGS. 1-4 and a surgical drape covering a portion of a patient's face, according to embodiments of the disclosure.
Figure 6:
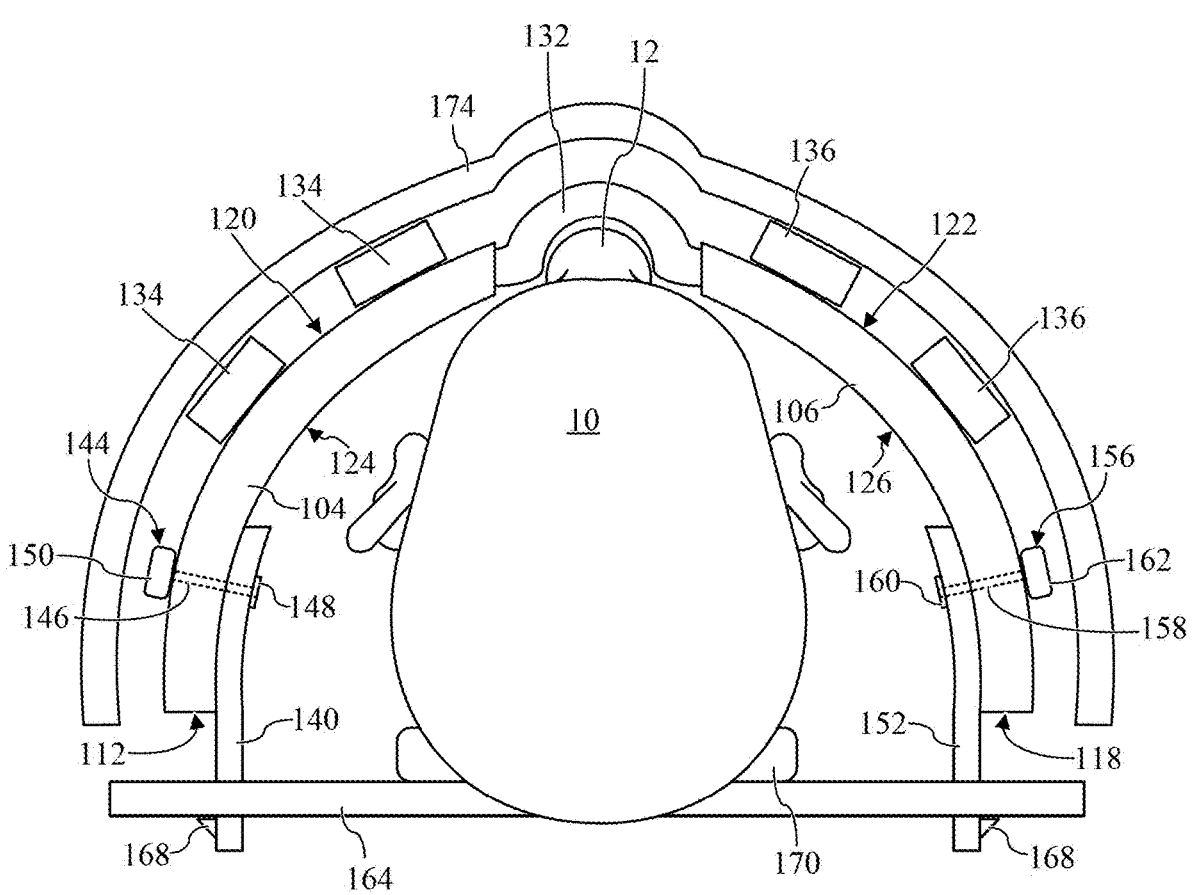
FIG. 6 shows a back view of the face shield system and patient of FIG. 5, according to embodiments of the disclosure.

Turning to FIGS. 5 and 6, a face shield system 172 (hereafter, "system 172") including face shield apparatus 100 of FIGS. 1-4 is shown. More specifically, FIG. 5 shows a top view of system 172 including face shield apparatus 100 and a surgical drape 174 at least partially covering a patient's face 10, while FIG. 6 shows a back view of system 172 including face shield apparatus 100 and a surgical drape 174 at least partially covering hey patient's face 10. It is understood that similarly numbered and/or named components may function in a substantially similar fashion. Redundant explanation of these components has been omitted for clarity.

As shown in FIGS. 5 and 6, surgical drape 174 of system 172 may be positioned over and may contact at least a portion of face shield apparatus 100. More specifically, surgical drape 174 may be positioned/disposed over and may contact/rest upon frame 102, first rib(s) 134, and second rib(s) 136, respectively. Additionally as shown, frame 102, first rib(s) 134, and second rib(s) 136 may support surgical drape 174, such that surgical drape 174 is positioned above, but does not contact patient's face 10 directly. Furthermore, and with reference to FIG. 6, maintaining frame 102 at the predetermined height, as discussed herein, may also prevent frame 102 from contacting patient's face 10. as shown, neither first curved member 104 nor second curved member 106 of frame 102 make contact patient's face 10. Moreover, and based on the adjustable shape or configuration, bridge 132 of face shield apparatus 100 may receive, be positioned adjacent to and/or contour around patient's nose 12, without contacting the patient. To maintain a sterile environment, as discussed herein, a portion of surgical drape 174 may extend beyond frame 102 of face shield apparatus 100, opposite rib(s) 134, 136, and may be taped directly to patient's face 10. Surgical drape 174 may be formed as any suitable surgical drape, cloth, towel, and/or material that may aid in maintaining sterile environments and/or isolating areas of the patient undergoing surgery/operations.

When performing ocular-based (e.g., eye, eyelid) and/or upper face surgeries on a patient, system 172 including face shield apparatus 100 and surgical drape 174 may be used to maintain a sterilized environment and/or isolate the area of the patient undergoing the surgery. Additionally, and because face shield apparatus 100 ensures surgical drape 174 does not contact a patient's face 10, the use of system 172 may provide improved access to other critical devices or systems involved in the surgical procedure. For example, where the patient is required to wear an oxygen mask around their mouth and/or nose, an anesthesiologist/nurse/operating room technician may more readily access the mask underneath surgical drape 174 and bridge 132/rib(s)134, 136 of face shield apparatus 100 as a result of surgical drape 174 being suspended above and not contacting patient's face 10. That is, surgical drape 174 may not rest upon patient's face 10 and/or the oxygen mask, but rather a space may exist between surgical drape 174 and the oxygen mask allowing for easier/improved access.

FIGS. 7-10 show additional non-limiting examples of face shield apparatus 100. It is understood that similarly numbered and/or named components may function in a substantially similar fashion. Redundant explanation of these components has been omitted for clarity.

Figure 7:
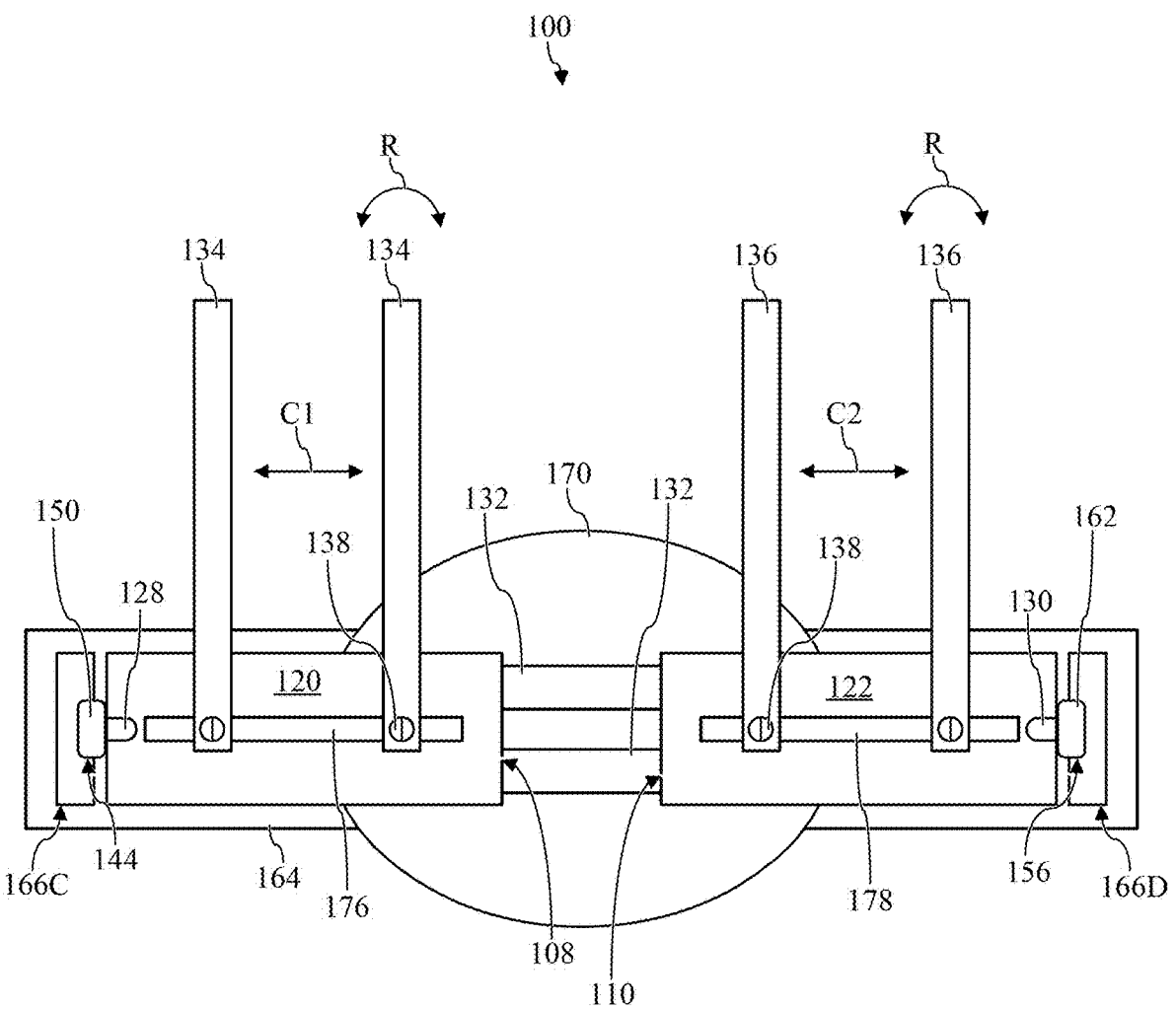
FIG. 7 shows a top view of a face shield apparatus, according to additional embodiments of the disclosure.

In the non-limiting example shown in FIG. 7, face shield apparatus 100 may also include a first track 176 and a second track 178 formed in frame 102. More specifically, first track 176 may be formed in outer surface 120 of first curved member 104. First track 176 may also be formed adjacent first end 108 of first curved member 104. Second track 178 may be formed in outer surface 122 of second curved member 106, and may be formed adjacent first end 110 of second curved member 106 as well. As shown in FIG. 7, ribs 134, 136 may be positioned within first track 176 or second track 178. That is, first rib(s) 134 may slidably engage and/or may be pivotably coupled within first track 176 formed in first curved member 104. Similarly, second rib(s) 136 may slightly engage and/or may be pivotably coupled within second track 178 formed in second curved member 106. In this non-limiting example, ribs 134, 136 may not only be pivotable or rotatable in a direction (R), but ribs 134, 136 may also be capable of moving in a direction (C1, C2) along the curvature of outer surface 120, 122 of first curved member 104/second curved member 106.

Figure 8:
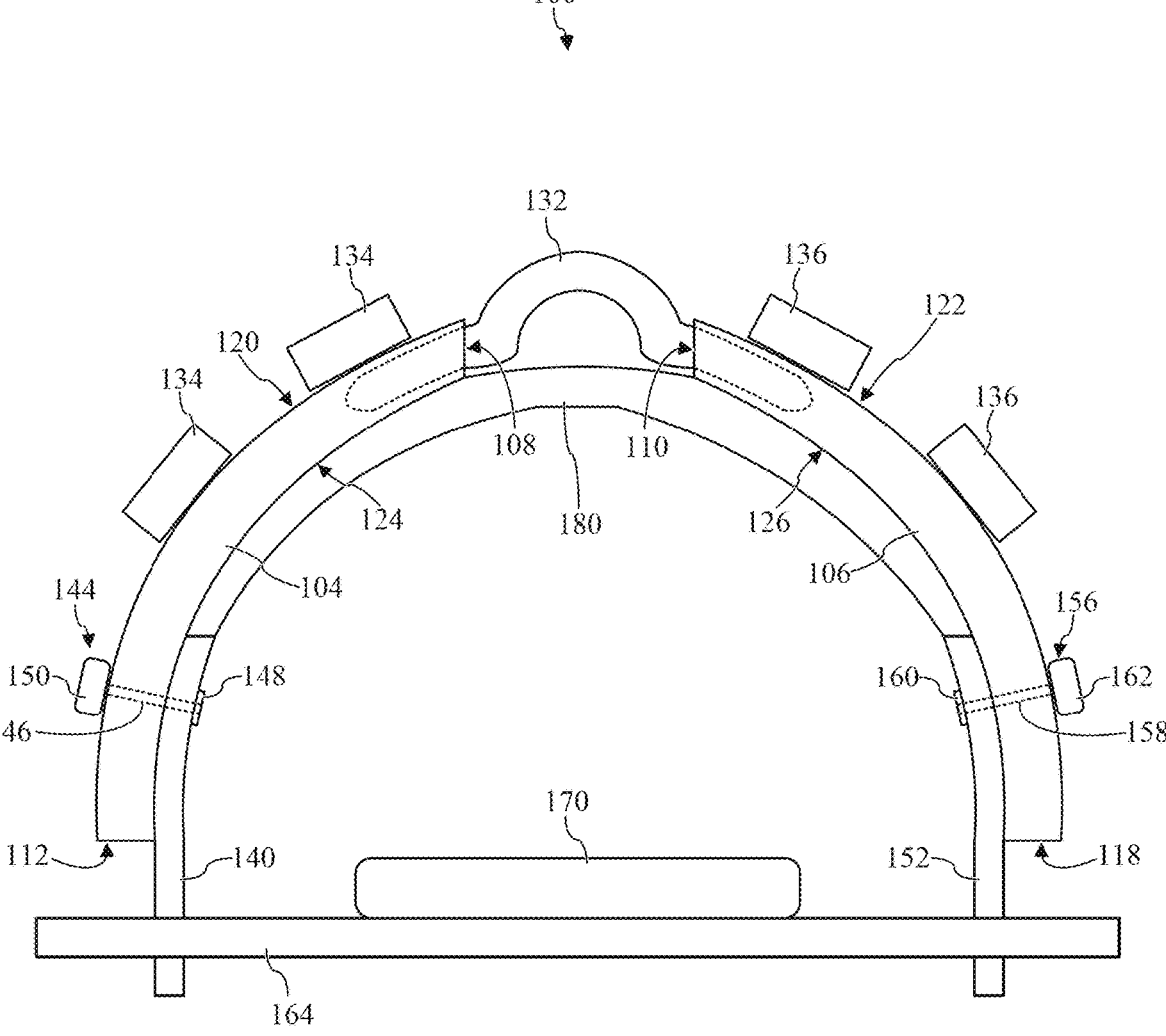
FIG. 8 shows a back view of a face shield apparatus, according to further embodiments of the disclosure.

In the non-limiting example shown in FIG. 8, first extension 140, second extension 152, and backing component 164 may be formed integral with one another. That is, first extension 140, second extension 152, and backing component 164 may all be formed as a single, unitary component or embodiment of face shield apparatus 100. In this example, first extension 140 and second extension 152 may be permanently fixed to backing component 164.

Additionally, as shown in FIG. 8, face shield apparatus 100 may include a pad 180. Pad 180 may be positioned on a portion of frame 102 and may extend toward backing component 164. More specifically, pad 180 may be positioned on at least a portion of inner surface 124 of first curved member 104 and at least a portion of inner surface 126 of second curved member 106. Distinct from non-limiting examples discussed herein (e.g., FIGS. 1-6), pad 180 of face shield apparatus 100 may contact a patient's face 10. That is, pad 180 may extend from frame 102 toward a patient's face 10 and may substantially contact and form a seal around patient's face 10. In this non-limiting example, pad 180 forming a seal around face 10 of the patient may improve sterilization practices and/or procedures. Pad 180 may be formed from any suitable material having substantially elastic and/or flexible properties to contour around the patient's face 10. For example, pad 180 may be formed as a medical gel pad.

A portion of bridge 132 of face shield apparatus 100 may also extend into frame 102. For example, and as shown in FIG. 8, bridge 132 may slidably extend into first curved member 104 and second curved member 106, adjacent first ends 108, 110. Bridge 132 may slightly extend into first curved member 104 and second curved member 106 to allow for adjustments in the size, shape, and/or height of bridge 132. Where the height of bridge 132 must be increased, more of bridge 132 may be pulled from and/or positioned outside of first curved member 104 and second curved member 106, respectively. Conversely, where the height and/or size of bridge 132 must be decreased or reduced, more of bridge 132 may be inserted or slid into first curved member 104 and second curved member 106, and less of bridge 132 may be exposed between first ends 108, 110 of first curved member 104 and second curved member 106. Because of its flexible and/or elastic properties, bridge 132 inserted or disposed within first curved member 104 or second curved member 106 may flex/contour about the curvature of each member of frame 102.

Figure 9:
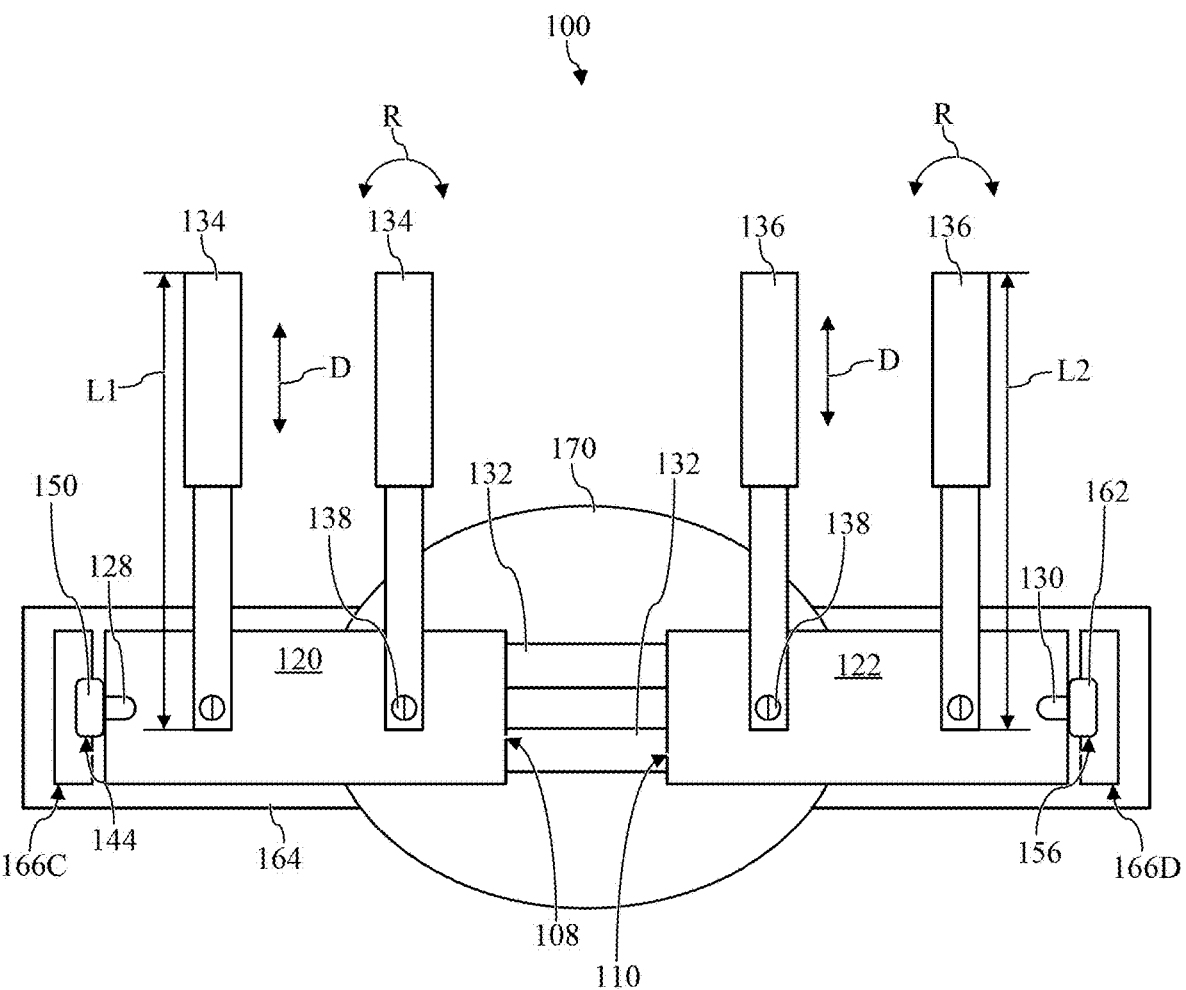
FIG. 9 shows a top view of a face shield apparatus, according to other embodiments of the disclosure.

Turning to FIG. 9, another non-limiting example of face shield apparatus 100 is shown. In the example, ribs 134, 136 may include adjustable lengths. More specifically, first rib(s) 134 may include a telescoping configuration or structure to adjust a first length (L1) of first rib(s) 134. Similarly, second rib(s) 136 may include a telescoping configuration or structure to adjust a second length (L2) of second rib(s) 136. Lengths (L1, L2) may be adjusted by sliding telescoping portions of rib(s) 134, 136 in a direction (D). As such, the length (L1, L2) of each rib 134, 136 included in face shield apparatus 100 may be (near) instantaneously adjusted by either lengthening or shortening desired ribs 134, 136.

Figure 10:
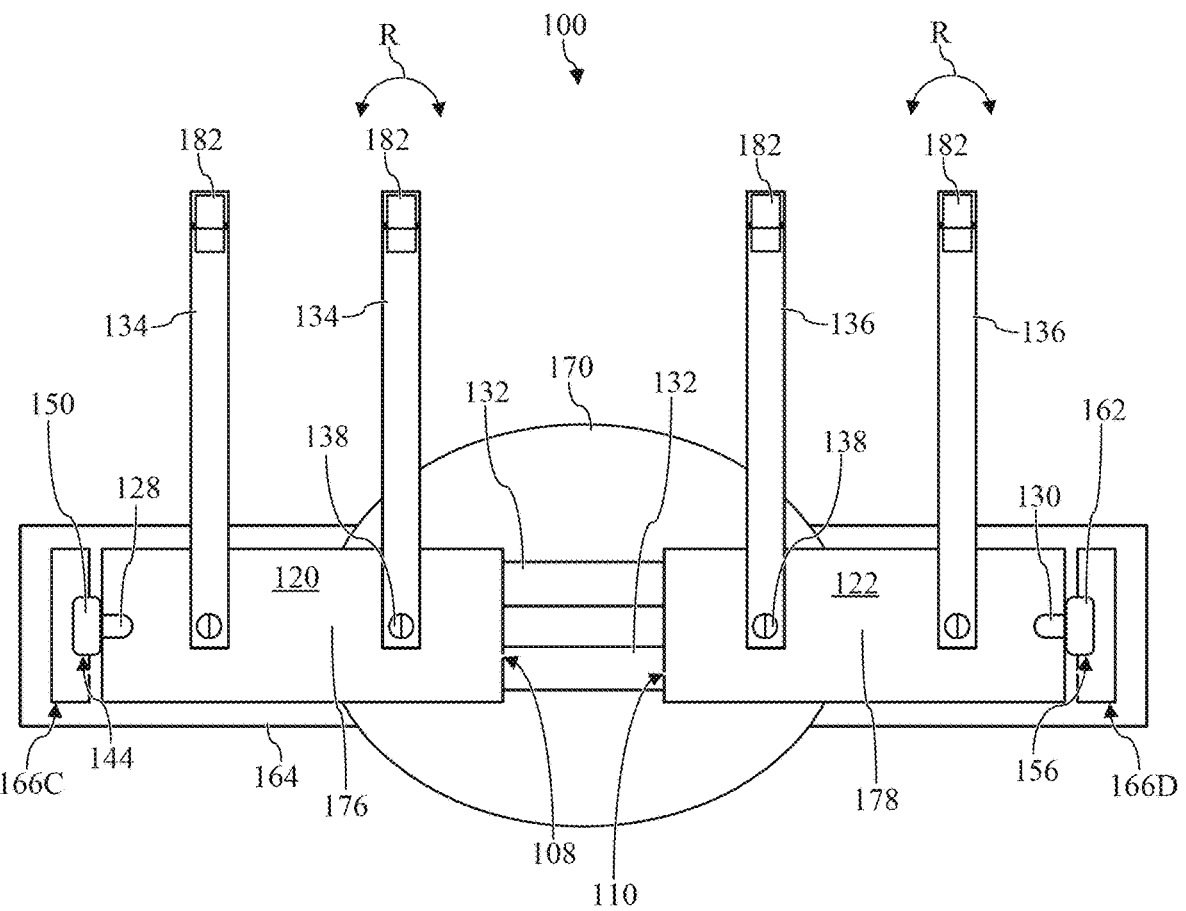
FIG. 10 shows a top view of a face shield apparatus, according to additional embodiments of the disclosure.

Face shield apparatus 100 shown in FIG. 10 may include additional components and/or devices. For example, each rib 134, 136 may include a clip 182 positioned thereon (e.g., at the tip, on top or underneath). More specifically, first rib(s) 134 and second rib(s) 136 may include clip 182 positioned on an end opposite frame 102. Clip 182 may be formed on an exposed surface of ribs 134, 136. Each clip 182 may receive and secure an end of surgical drape 174 disposed over frame 102, as discussed herein. Clip 182 may be formed as any suitable compression device that may secure and/or supply a force to surgical drape 174 to maintain its position on frame 102 a face shield apparatus 100. Although shown as being positioned on ribs 134, 136, it is understood that additional portions or components of face shield apparatus 100 may include clips 182 as well. In another non-limiting example (not shown) clips 182 may be positioned on and/or coupled to first curved member 104 and second curved member 106 of frame 102. In this non-limiting example, clips 182 positioned on first curved member 104 and second curved member 106 may aid in securing surgical drape 174 to frame 102 of face shield apparatus 100 when performing the medical procedure, as discussed herein. Furthermore, although shown at being formed on an end opposite frame 102, it is understood that clip may be formed in other distinct portions of ribs 134, 136. For example, clip 182 may be formed at a midpoint of ribs 134, 136, on a top surface (as shown), or an underside/undersurface (e.g., adjacent a patient's face).

Figure 11A:
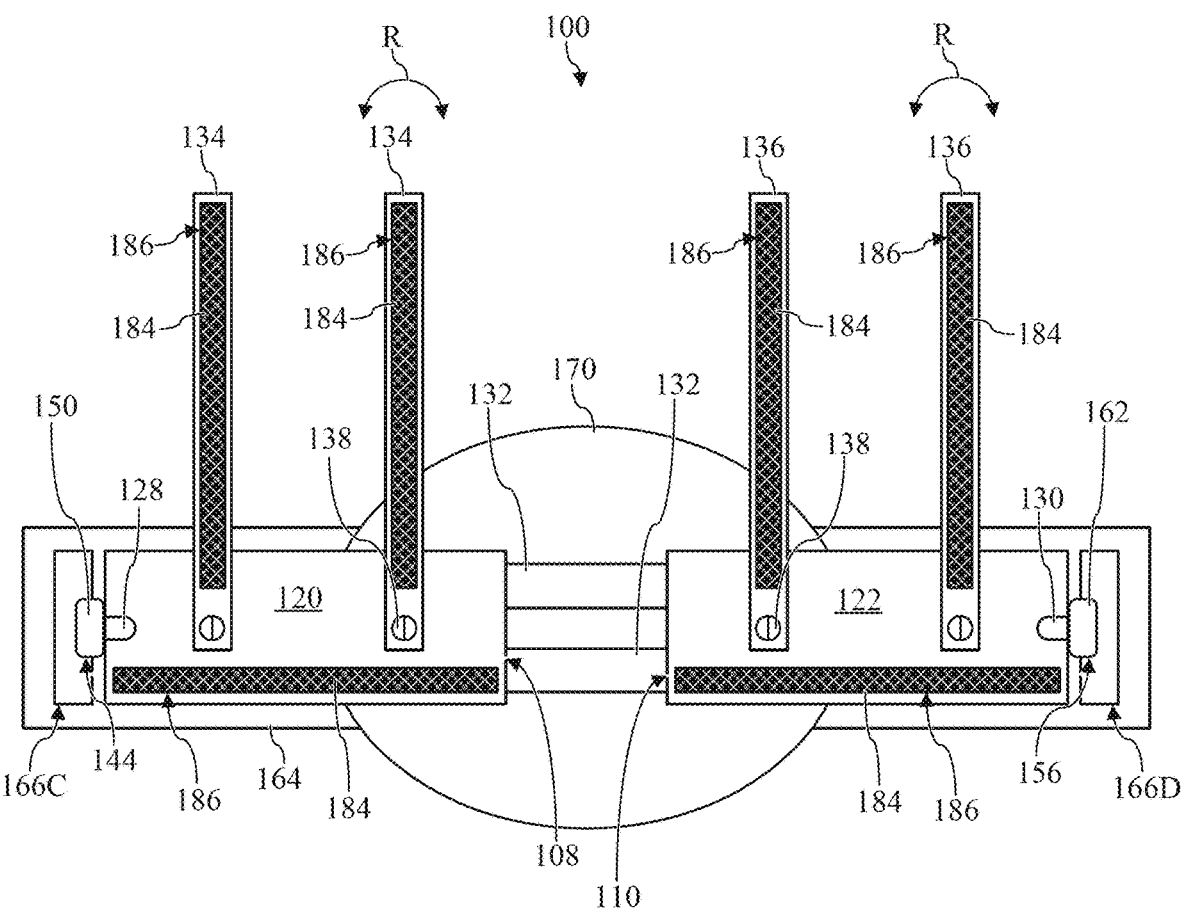
FIG. 11A shows a top view of a face shield apparatus of a face shield system, according to embodiments of the disclosure.
Figure 11B:
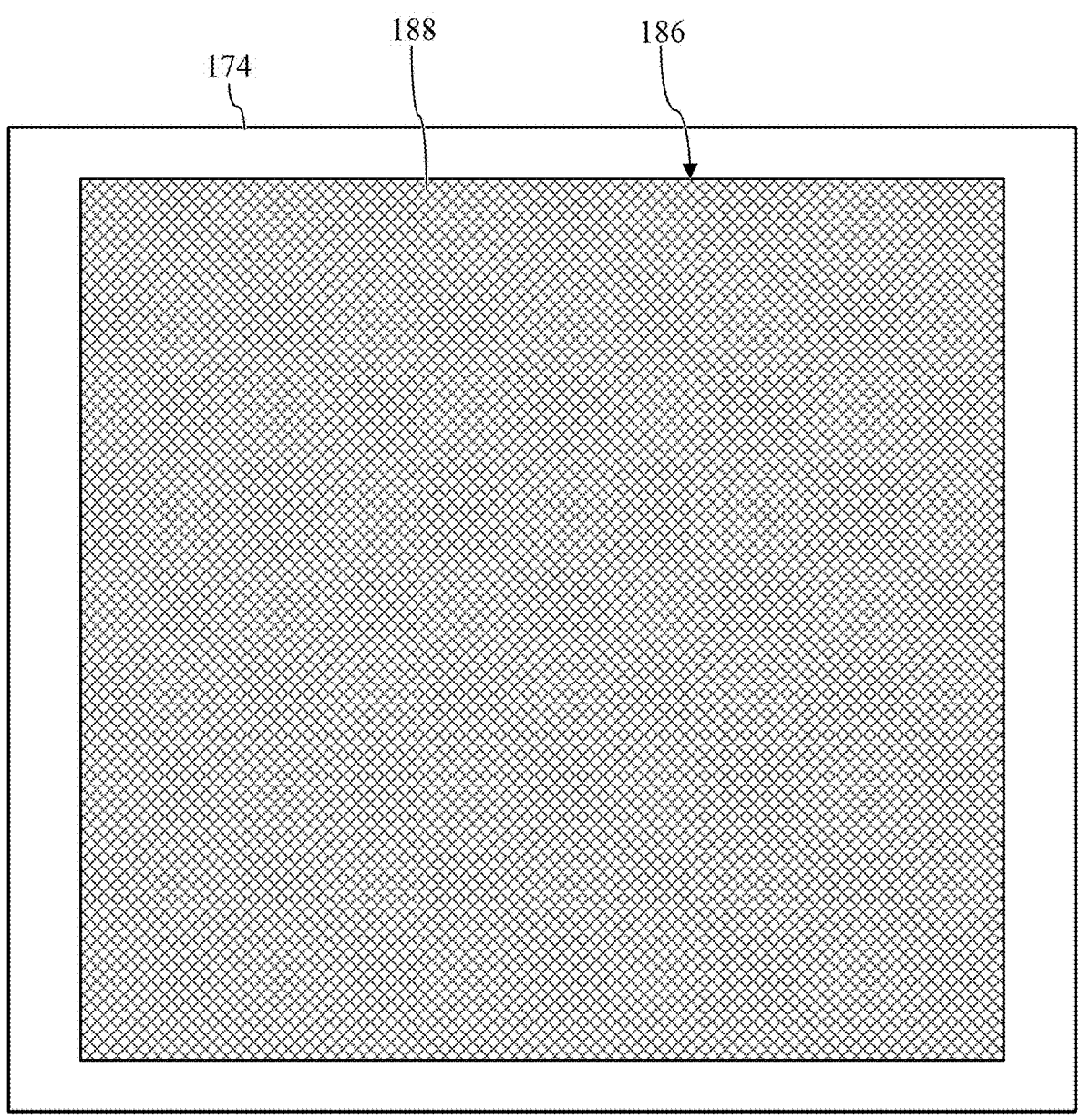
FIG. 11B shows a bottom view of a surgical drape included in the face shield system of FIG. 12A, according to embodiments of the disclosure.

FIGS. 11A and 11B show various views of system 172 including face shield apparatus 100 (FIG. 11A) and surgical drape 174 (FIG. 11B). In the non-limiting example of system 172, face shield apparatus 100 may include additional components formed thereon. For example, and as shown in FIG. 11A, first rib(s) 134 and second rib(s) 136 of face shield apparatus 100 may include a first portion 184 of a hook-and-loop fastener assembly 186—commonly referred to as Velcro®. That is, each of first rib(s) 134 and second rib(s) 136 may include first portion 184 (e.g., hook portion) of hook-and-loop fastener assembly 186 that may aid in securing surgical drape 174 to frame 102. Additionally in the non-limiting example, frame 102, and more specifically first curved member 104 and second curved member 106, may include first portion 184 of hook-and-loop fastener assembly 186 as well. Turning to FIG. 11B, surgical drape 174 may include a second portion 188 of hook-and-loop fastener assembly 186. More specifically, a bottom surface of surgical drape 174 may include second portion 188 of hook-and-loop fastener assembly 186 that may substantially cover the majority (e.g., greater than 50%) of the bottom surface. Second portion 188 of hook-and-loop fastener assembly 186 formed on surgical drape 174 may correspond to and/or may be configured to interact with first portion 184 of hook-and-loop fastener assembly 186 formed on face shield apparatus 100. In the non-limiting example, when surgical drape 174 is disposed over face shield apparatus 100, first portion 184 and second portion 188 of hook-and-loop fastener assembly 186 may interact and/or may be releasably coupled to one another.

Figure 12A:
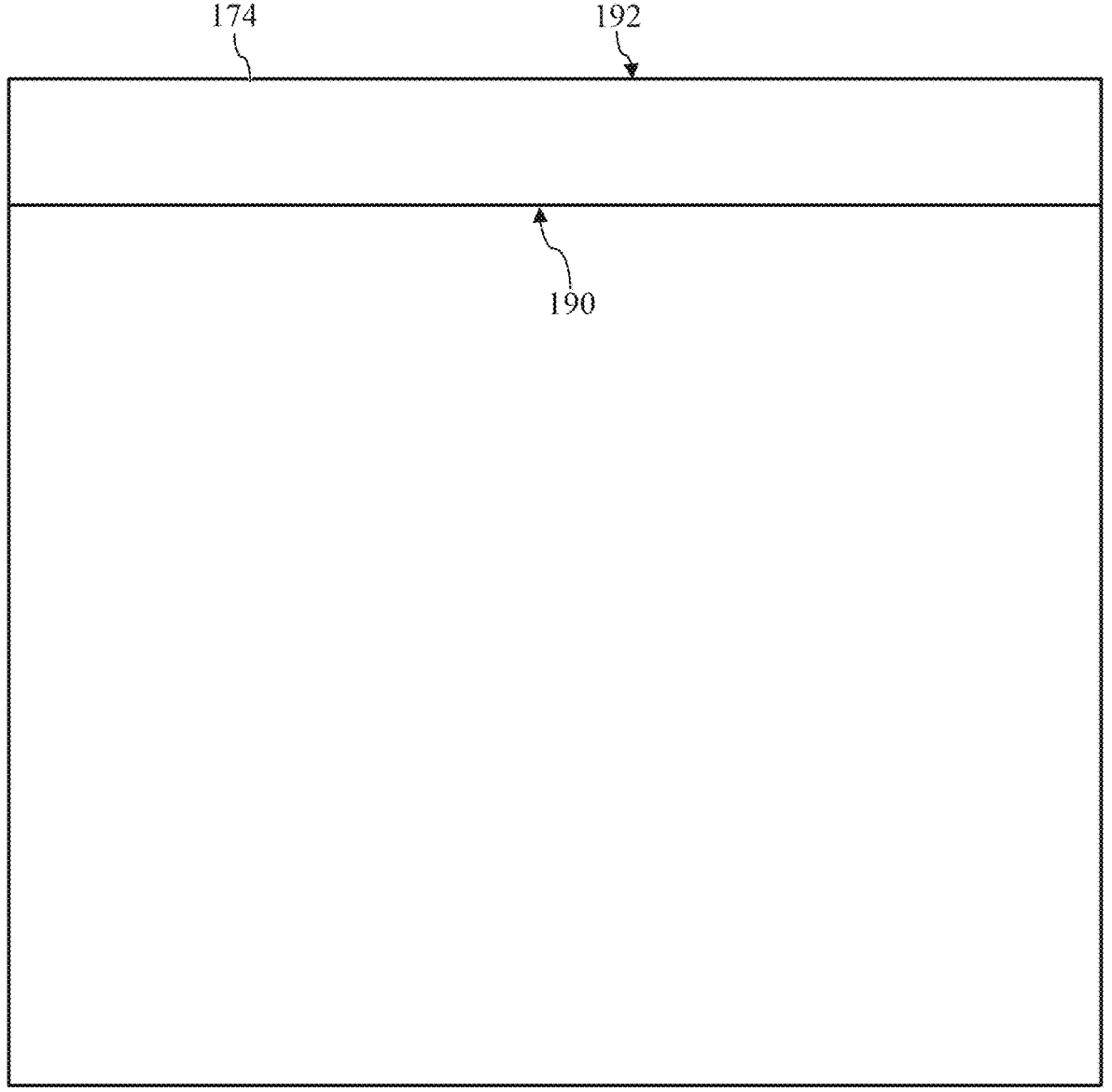
FIG. 12A shows a bottom view of a surgical drape included in a face shield system, according to additional embodiments of the disclosure.
Figure 12B:
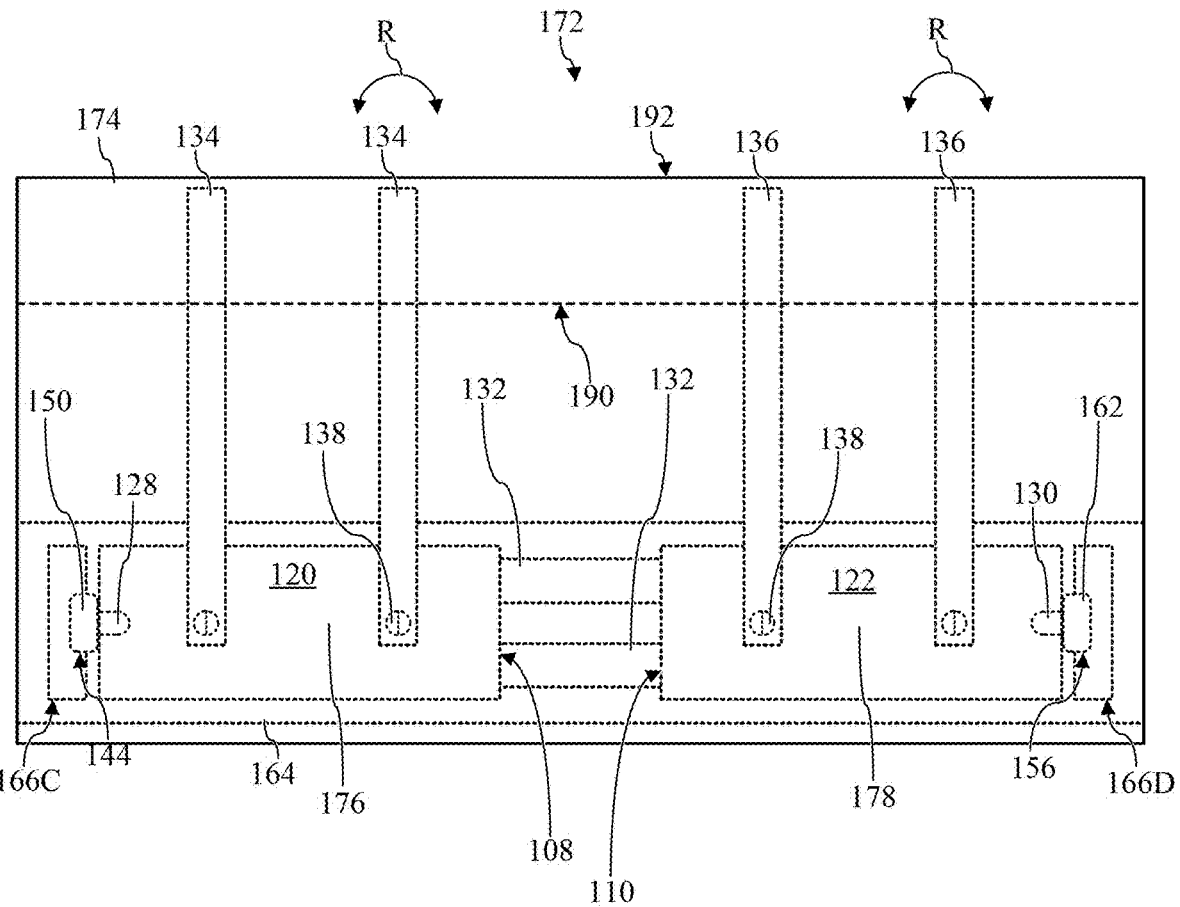
FIG. 12B shows a top view of a face shield apparatus and the surgical drape of FIG. 12A of the face shield system, according to embodiments of the disclosure.
Figure 13A:
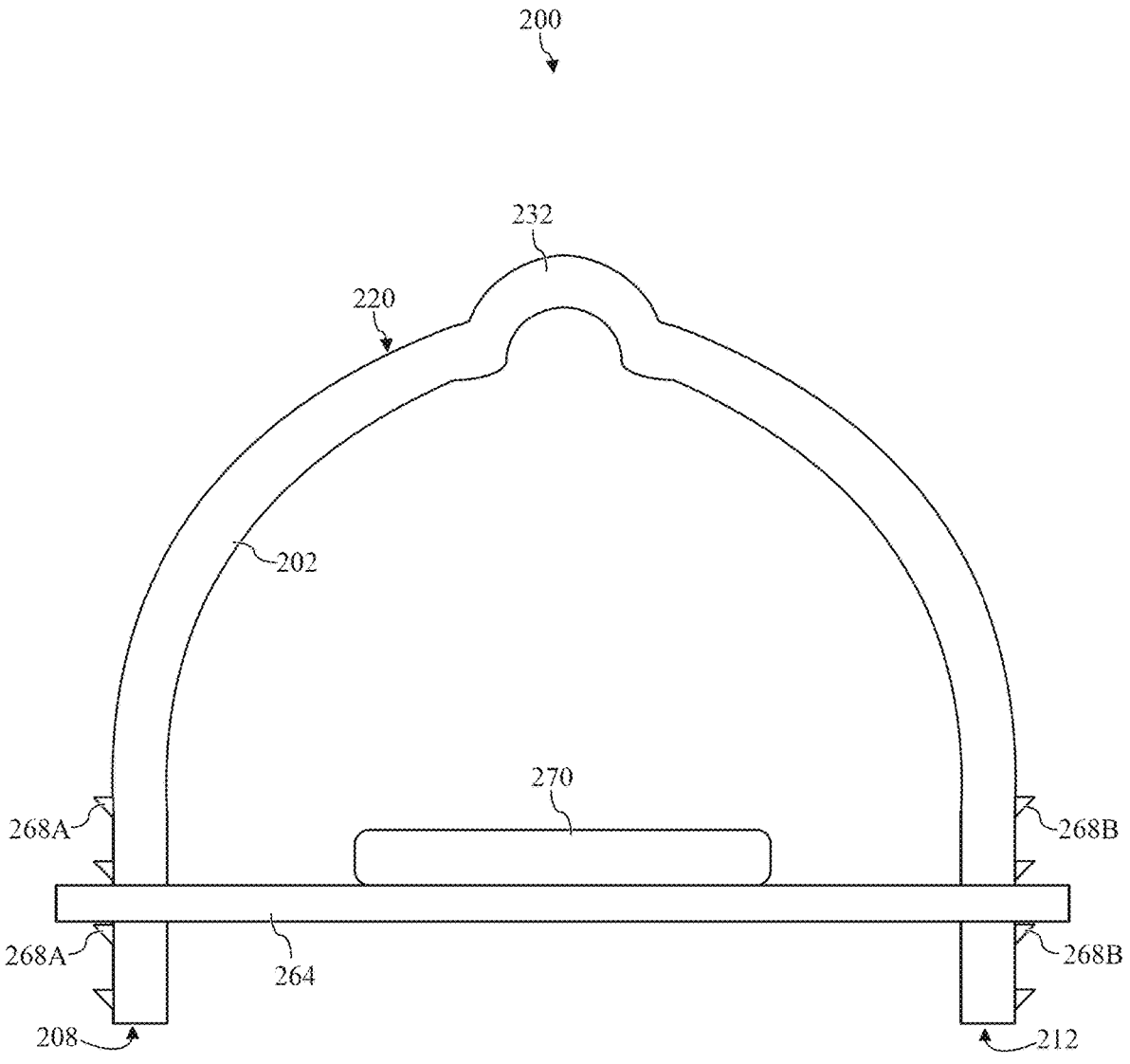
FIG. 13A shows a back view of a face shield apparatus, according to another embodiment of the disclosure.
Figure 13B:
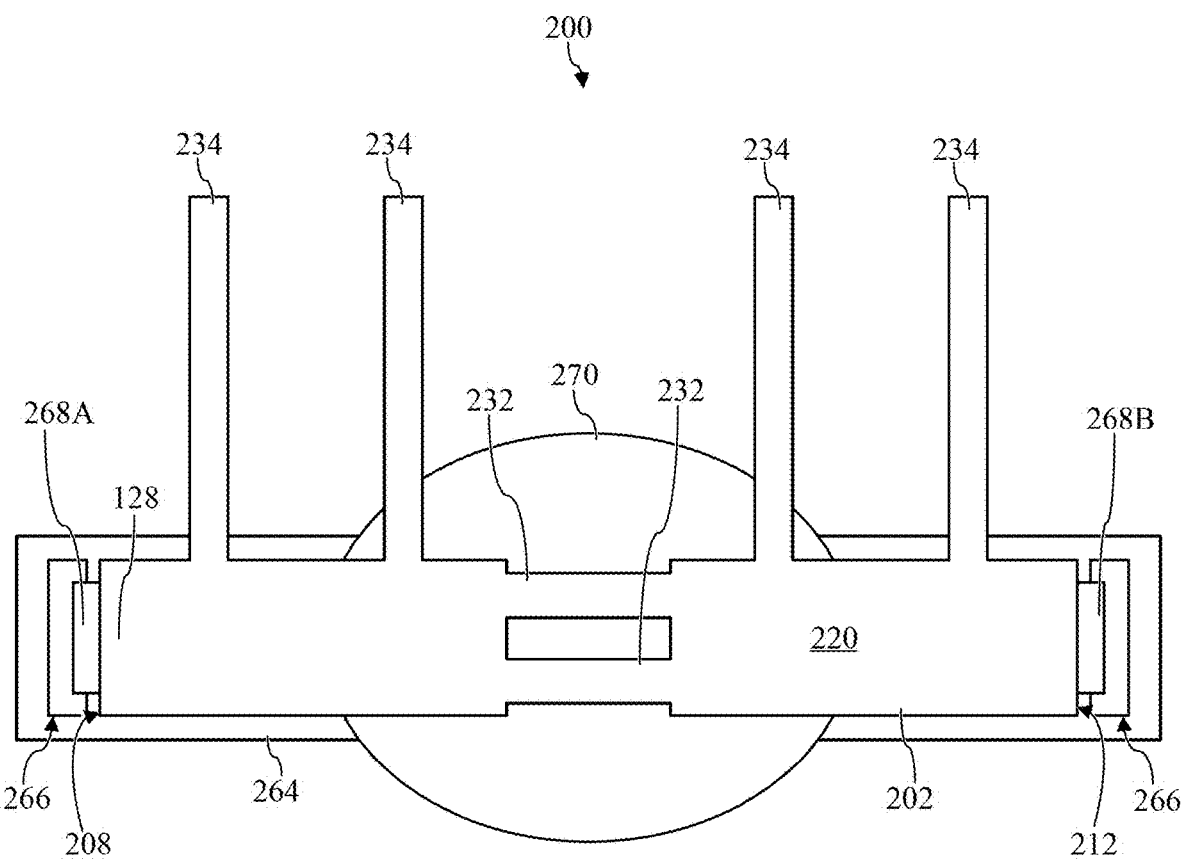
FIG. 13B shows a top view of the face shield apparatus of FIG. 13A, according to embodiments of the disclosure.

FIGS. 12A and 12B show another non-limiting example of system 172 including surgical drape 174 (FIG. 12A) and face shield apparatus 100 (FIG. 12B). In the non-limiting example, surgical drape 174 may include at least one pocket 190 formed on an end 192. More specifically, and as shown in FIG. 12A, a portion of surgical drape 174 may be folded onto itself at end 192 and at least the edges may be bonded (e.g., glued, sewed, etc.) to form pocket 190. Pocket 190 may receive at least a portion of each of first rib(s) 134 and second rib(s) 136 of face shield apparatus 100. Turning to FIG. 12B, ribs 134, 136 extending from first curved member 104/second curved member 106 may extend into and/or be received by pocket 190 formed in surgical drape 174. The formation of pocket 190 in surgical drape 174 may secure surgical drape 174 to face shield apparatus 100 and/or may prevent surgical drape 174 from undesirably sliding or moving during the surgical procedure.

turning to FIGS. 13A and 13B, another non-limiting example of face shield apparatus 200 is shown. It is understood that similarly numbered and/or named components may function in a substantially similar fashion. Redundant explanation of these components has been omitted for clarity. In this non-limiting example, components or portions not including backing component 164 may be integrally formed. That is, face shield apparatus 200 may include curved frame 202 including first end 208 and second end 212 positioned opposite first end 208. Additionally, curved frame 202 may include outer surface 220 extending between first end 208 and second end 212. Furthermore, and as shown in FIGS. 13A and 13B curved frame 202 may include a bridge 232 formed between first end 208 and second end 212. Finally, curved frame 202 may include a plurality of ribs 234 extending beyond and positioned substantially parallel to outer surface 220 of curved frame 202. In this example, and as shown, each of bridge 232 and ribs 234 may be formed integral with curved frame 202 such that all portions/features of curved frame 202 are included in a single, unitary body. Additionally, as a result of ribs 234 being formed integral with curved frame 202, ribs 234 may be static and/or may not be capable of rotating on curved frame 202 (compare with FIG. 2).

In the non-limiting example, face shield apparatus 200 may also include backing component 264 that may be substantially similar to backing component 164 discussed herein. However, because curved frame 202 is formed as a unitary/integral body (and does not include extensions 140, 152) backing component 264 may be releasably coupled to first end 208 and second end 212 of curved frame 202. Backing component 264 may include at least two openings 266 that may receive one of first end 208 and second end 212 of curved frame 202. To aid in the retention of curved frame 202 and/or to releasably couple curved frame 202 to backing component 264, curved frame 202 may also include a first plurality of ratchet style coupling components 268A and a second plurality of ratchet style coupling components 268B. In the non-limiting example shown in FIGS. 13A and 13B, the first plurality of ratchet style coupling components 268A and the second plurality of ratchet style coupling components 268B may be formed on outer surface 220 of curved frame 202. First ratchet style coupling components 268A may also be formed adjacent first end 208 of curved frame 202, which second ratchet style coupling components 268B may be formed adjacent second end 212. As similarly discussed herein with respect to ratchet style coupling component 168 (see, FIGS. 1-4), Ratchet style coupling components 268A, 268B may pass through openings 266 of backing component 264 to releasably couple and/or secure curved frame 202 to backing component 264. A flat shelf of each coupling component 268 may abut or contact backing component 264, adjacent openings 266 to prevent the undesired uncoupling of curved frame 202 and backing component 164.

Distinct from the non-limiting examples discussed herein, the first plurality of ratchet style coupling components 268A and the second plurality of ratchet style coupling components 268B may also aid in adjusting the height of curved frame 202. That is, each of the plurality of ratchet style coupling components 268A, 268B may determine a height of curved frame 202. In the non-limiting example shown in FIGS. 13A and 13B, the more coupling components 268A, 268B that pass-through openings 266 formed through backing component 264, the lower or smaller the height of curved frame 202.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" as applied to a particular value of a range applies to both values, and unless otherwise dependent on the precision of the instrument measuring the value, may indicate+/–10% of the stated value(s).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:
1. A face shield apparatus, comprising:
a frame including a first curved member and a second curved member positioned opposite the first curved member, each of the first curved member and the second curved member including:
a first end;
a second end positioned opposite the first end; and
an outer surface extending between the first end and the second end;
a bridge extending between the first end of the first curved member and the first end of the second curved member;
at least one first rib rotatably coupled to the outer surface of the first curved member, the at least one first rib extending beyond and substantially parallel to the outer surface of the first curved member;
at least one second rib rotatably coupled to the outer surface of the second curved member, the at least one second rib extending beyond and substantially parallel to the outer surface of the second curved member;
a first extension coupled to the first curved member, adjacent the second end of the first curved member;

14 a second extension coupled to the second curved member, adjacent the second end of the second curved member; and
a backing component releasably coupled to the first extension and the second extension, the backing component including:
at least two openings, the at least two openings receiving one of the first extension or the second extension.
2. The face shield apparatus of claim 1, wherein each of the first curved member and the second curved member of the frame includes:
an aperture extending through the outer surface, the aperture formed adjacent the second end.
3. The face shield apparatus of claim 2, wherein each of the first extension and the second extension includes:
a hole extending therethrough,
wherein the hole of the first extension is aligned with the aperture formed through the first curved member, and
the hole of the second extension is aligned with the aperture formed through the second curved member.
4. The face shield apparatus of claim 3, further comprising:
a first fastener extending through the hole of the first extension and the aperture of the first curved member, the first fastener allowing for adjustment in a height of the frame and releasably coupling the first extension to the first curved member; and
a second fastener extending through the hole of the second extension and the aperture of the second curved member, the second fastener allowing for adjustment in the height of the frame and releasably coupling the second extension to the second curved member.
5. The face shield apparatus of claim 1, wherein the bridge slidably extends into the first curved member and into the second curved member to adjust a height of the bridge.
6. The face shield apparatus of claim 1, wherein the bridge is formed from a flexible material.
7. The face shield apparatus of claim 1, wherein:
the at least one first rib includes a telescoping configuration to adjust a first length of the at least one first rib, and
the at least one second rib includes a telescoping configuration to adjust a second length of the at least one second rib.
8. The face shield apparatus of claim 1, further comprising:
a cushion positioned on the backing component, between the at least two openings formed therein.
9. The face shield apparatus of claim 1, further comprising:
a first track formed in the outer surface of the first curved member, adjacent the first end,
wherein the at least one first rib slidably engages the first track formed in the first curved member; and
a second track formed in the outer surface of the second curved member, adjacent the first end,
wherein the at least one second rib slidably engages the second track formed in the second curved member.
10. The face shield apparatus of claim 1, wherein the at least one first rib and the at least one second rib includes:
a clip positioned on an end opposite the frame, the clip receiving and securing a surgical drape disposed over the frame.
11. The face shield apparatus of claim 1, wherein the first extension, the second extension, and the backing component are integrally formed.

12. The face shield apparatus of claim 1, further comprising:

a pad positioned on at least a portion of an inner surface of each of the first curved member and the second curved member, the pad configured for contacting and forming a seal around a patient's face.

13. The face shield apparatus of claim 1, further comprising:

at least one ratchet-style coupling component formed on both the first extension and the second extension, opposite the second end of the first curved member and the second curved member, respectively, wherein the at least one ratchet-style coupling component passes through one of the at least two openings of the backing component to couple the first curved member and the second curved member to the backing component.

14. The face shield apparatus of claim 1, the backing component is formed from a substantially flexible material.

15. A face shield system, comprising:

a face shield apparatus including:

a frame including a first curved member and a second curved member positioned opposite the first curved member, each of the first curved member and the second curved member including:

a first end;

a second end positioned opposite the first end; and an outer surface extending between the first end and the second end;

a bridge extending between the first end of the first curved member and the first end of the second curved member;

at least one first rib rotatably coupled to the outer surface of the first curved member, the at least one first rib extending beyond and substantially parallel to the outer surface of the first curved member;

at least one second rib rotatably coupled to the outer surface of the second curved member, the at least one second rib extending beyond and substantially parallel to the outer surface of the second curved member;

a first extension coupled to the first curved member, adjacent the second end of the first curved member;

a second extension coupled to the second curved member, adjacent the second end of the second curved member; and a backing component releasably coupled to the first extension and the second extension, the backing component including:

at least two openings, the at least two openings receiving one of the first extension or the second extension; and a surgical drape positioned over and contacting at least the frame, the at least one first rib, and the at least one second rib, respectively.

16. The face shield system of claim 15, wherein each of the at least one first rib and the at least one second rib of the face shield apparatus further includes a first portion of a hook-and-loop fastener assembly formed thereon.

17. The face shield system of claim 16, wherein the surgical drape further includes a second portion of the hook-and-loop fastener assembly formed thereon, the second portion of the hook-and-loop fastener assembly corresponding to the first portion of the hook-and-loop fastener assembly formed on the at least one first rib and the at least one second rib of the face shield apparatus.

18. The face shield system of claim 15, wherein the surgical drape includes a pocket formed on an end, the pocket receiving at least a portion of each of the at least on first rib and the at least one second rib of the face shield apparatus.

19. A face shield apparatus, comprising:

a curved frame including:

a first end;

a second end positioned opposite the first end;

an outer surface extending between the first end and the second end;

a bridge formed between the first end and the second end; and a plurality of ribs extending beyond and substantially parallel to the outer surface of the curved frame; and a backing component releasably coupled to the first end of the curved frame and the second end of the curved frame, the backing component including:

at least two openings, the at least two openings receiving one of the first end of the curved frame and the second end of the curved frame.

20. The face shield apparatus of claim 19, further comprising:

a first plurality of ratchet-style coupling components formed on the outer surface of the curved frame, adjacent the first end, the first plurality of ratchet-style coupling components passing through a first opening of the at least two openings of the backing component to adjustably couple the curved frame to the backing component; and a second plurality of ratchet-style coupling components formed on the outer surface of the curved frame, adjacent the second end, the second plurality of ratchet-style coupling components passing through a second opening of the at least two openings of the backing component to adjustably couple the curved frame to the backing component.

* * * * *